(12) United States Patent
Klunder

(10) Patent No.: US 8,158,398 B2
(45) Date of Patent: Apr. 17, 2012

(54) MICROELECTRONIC SENSOR DEVICE

(75) Inventor: Derk J. W. Klunder, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/810,022

(22) PCT Filed: Dec. 18, 2008

(86) PCT No.: PCT/IB2008/055417
§ 371 (c)(1),
(2), (4) Date: Jun. 22, 2010

(87) PCT Pub. No.: WO2009/083884
PCT Pub. Date: Jul. 9, 2009

(65) Prior Publication Data
US 2010/0276577 A1    Nov. 4, 2010

(30) Foreign Application Priority Data

Dec. 26, 2007   (EP) .................................... 07301744

(51) Int. Cl.
*G01N 21/31* (2006.01)
*G01N 21/64* (2006.01)
*G02B 27/56* (2006.01)

(52) U.S. Cl. .... 435/164; 250/200; 250/216; 250/237 G; 250/237 R; 250/458.1; 359/558

(58) Field of Classification Search ............ 436/164; 359/558, 487, 483, 486, 485; 250/200, 216, 250/237 G, 237 R, 459.4, 458.1
See application file for complete search history.

(56) References Cited

U.S. PATENT DOCUMENTS
2006/0034729 A1   2/2006   Poponin

FOREIGN PATENT DOCUMENTS
| EP | 0286195 A2 | 10/1988 |
|---|---|---|
| WO | 2007072293 A2 | 6/2007 |
| WO | 2007072415 A2 | 6/2007 |
| WO | 2007072418 A2 | 6/2007 |
| WO | 2009040721 A1 | 4/2009 |
| WO | 2009040746 A1 | 4/2009 |

OTHER PUBLICATIONS

Lin et al: "Surface Plasmon Resonance Biosensors With Subwavelength Grating Waveguide": Plasmonics in Biology and Medicine IV, Proceedings of SPIE, vol. 6450, Jan. 2007, pp. 1-8.

*Primary Examiner* — Christine T Mui

(57) ABSTRACT

An optical device provides evanescent radiation, in response to incident radiation, in a detection volume for containing a target component in a medium. The detection volume has at least one in-plane dimension (W1) smaller than a diffraction limit. The diffraction limit is defined by the radiation wavelength and the medium. The evanescent radiation is provided by aperture defining structures having a smallest in plane aperture dimension (W1) smaller than the diffraction limit. The detection volume is provided between the aperture defining structures. The aperture defining structures further define a largest in plane aperture dimension (W2). The largest in plane aperture dimension is larger than the diffraction limit. A source is provided for emitting a beam of radiation having a wavelength incident at the optical device and having a direction of incidence non parallel to an out of plane normal direction, for providing the evanescent radiation in the detection volume, in response to the radiation incident at the optical device. The plane of incidence may be parallel to the largest in plane aperture dimension.

12 Claims, 6 Drawing Sheets

MICROELECTRONIC SENSOR DEVICE

FIELD OF THE INVENTION

The invention relates to a microelectronic sensor device for the detection of target components.

BACKGROUND OF THE INVENTION

In an inhomogeneous assay, the concentration of a targeted bio-molecule can be determined by measuring the surface concentration of the targeted bio-molecule or beads [that are representative for the targeted bio molecule] bound at the sensor surface. As an example, one can think of a competitive assay where the binding surface (substrate) is covered with target molecules. The beads may be covered with specific [for the target molecule] antibodies and are dispersed in a fluid that contains the target molecules. The free target molecule in the sample competes with the immobilized target molecule on the sensor surface for binding to the antibody-coated bead. In case of a low concentration, the chance that an antibody binds with a target molecule at the sensor surface is higher than the chance that an antibody binds with a target molecule in the solution. By measuring the surface concentration of beads that are bound at the substrate, one can determine the concentration of the target molecule. Accurate measurement of the concentration however requires a highly surface specific detection scheme that is sufficiently insensitive for beads in the solution. A prior art sensor utilizes an evanescent field mode that is generated by illuminating sub diffraction limited apertures on a sensor surface, in particular, the so called wire grid, which has aperture defining structure defining a largest in plane aperture dimension larger than the diffraction limit and a smallest in plane aperture dimension smaller than the diffraction limit. Typically, the detection volume of the beads is provided between said aperture defining structures—so that the beads through electromagnetical interaction with the evanescent field mode, provide a detectable radiation—for instance, luminescence radiation or a change of reflectivity/transmissivity of the sensor due to the presence of beads. Generally, the sensitivity of a wire grid biosensor depends on the fraction of the input/excitation power that is coupled into the evanescent detection volume. In illumination modes wherein the illumination has an angle with respect to the surface normal, the power that is coupled into the detection volume will be reduced. A desire exists to increase the excitation efficiency, without needing to utilize higher intensities for the detection of target components.

SUMMARY OF THE INVENTION

According to an aspect, an optical device is provided for providing evanescent radiation, in response to incident radiation, in a detection volume for containing a target component in a medium, the detection volume having at least one in-plane dimension (W1') smaller than a diffraction limit. The diffraction limit is defined by the radiation wavelength and the medium; the evanescent radiation is provided by aperture defining structures having a smallest in plane aperture dimension W1 smaller than the diffraction limit, and the detection volume is provided between said aperture defining structures. The aperture defining structures in addition define a largest in plane aperture dimension W2; wherein said largest in plane aperture dimension is larger than the diffraction limit. An optical guiding device is provided for guiding a beam of radiation having a wavelength to have a direction of incidence different from an out of plane normal direction, for providing evanescent radiation in the detection volume, in response to the radiation incident at the optical device. The optical guiding device is arranged to provide a plane of incidence being along the largest in plane aperture dimension and the out of plane normal direction.

In another aspect there is provided a method for detecting target component in an detection volume formed in an aperture is provided, comprising: emitting a beam of radiation having a wavelength incident at the optical device and having direction of incidence different from an out of plane normal direction and providing evanescent radiation, in response to incident radiation, in a detection volume for containing a target component in a medium, the detection volume having at least one in-plane dimension (W1) smaller than a diffraction limit, the diffraction limit defined by the radiation wavelength and the medium, wherein the evanescent radiation is provided by aperture defining structures having a smallest in plane aperture dimension W1 smaller than the diffraction limit, and wherein the detection volume is provided between said aperture defining structures, wherein the aperture defining structures in addition define a largest in plane aperture dimension W2; wherein said largest in plane aperture dimension is larger than the diffraction limit. Radiation from the target component present in the detection volume is detected, in response to the emitted incident radiation from the source. The plane of incidence is arranged along the largest in plane aperture dimension and the out of plane normal direction.

These and other aspects of the invention will be apparent from and elucidated with reference to the embodiment(s) described hereinafter.

DETAILED DESCRIPTION OF EMBODIMENTS

Figure 1:
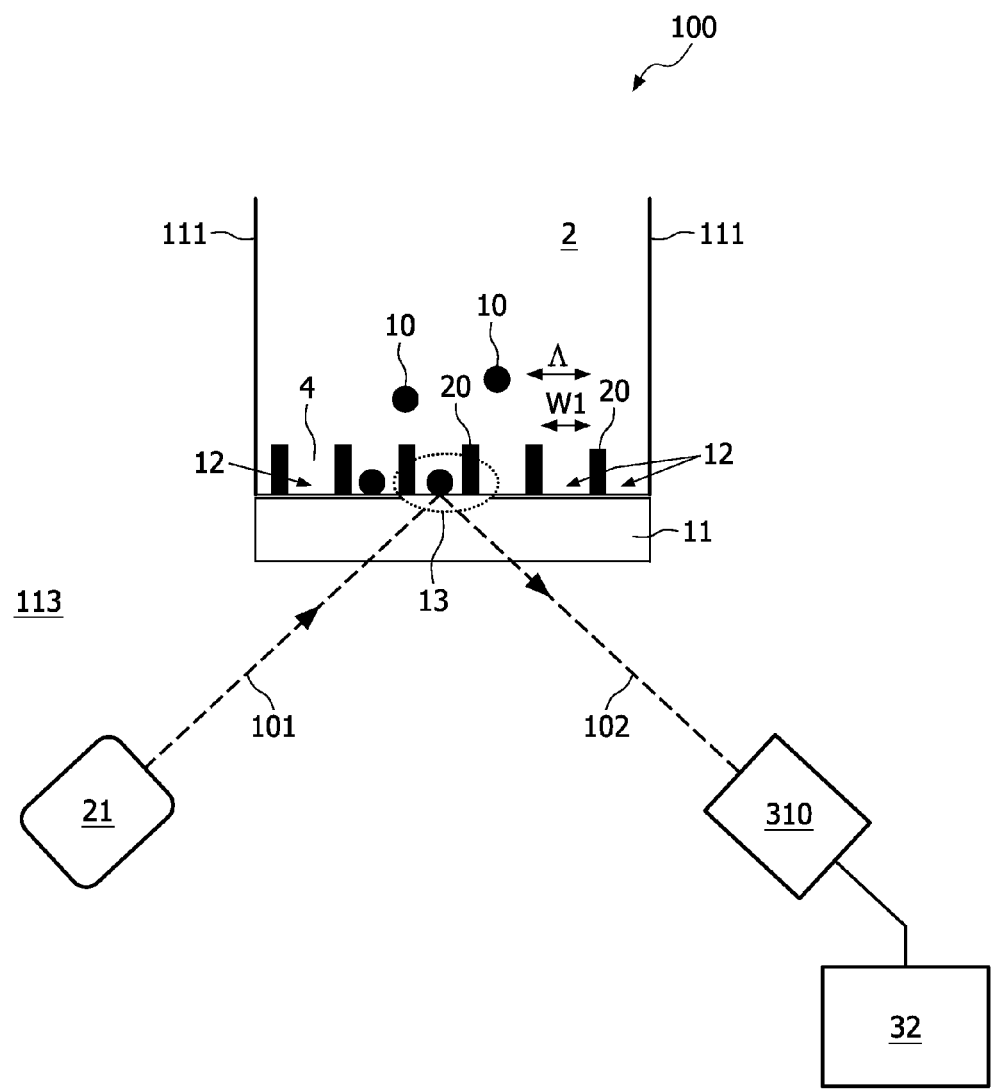
FIG. 1 shows a setup of a microelectronic sensor device.

The microelectronic sensor device according to the present invention may serve for the qualitative or quantitative detection of target components, wherein the target components may for example be biological substances like biomolecules, complexes, cell fractions or cells. The term "label and/or particle" shall denote a particle (atom, molecule, complex, nanoparticle, microparticle etc.) that has some property (e.g. optical density, magnetic susceptibility, electrical charge). For example, the target components are luminescent or may define an index of refraction different from larger than the medium index of refraction that can be detected, thus indirectly revealing the presence of the associated target component.

A "target component" and a "label particle" may be identical. In addition, the microelectronic sensor device, according to an aspect of the invention may comprise the following components:

a) The sensor is provided with a plurality of aperture defining structures having a first smallest in plane aperture dimension (W1) smaller than a diffraction limit, the diffraction limit (Wmin) defined by a medium for containing the target components: by a:

$$W\text{min} = \lambda / (2 * n\text{medium}) \quad (1)$$

with λ the wavelength in vacuum and $n_{medium}$ the refractive index of the medium in front of the wire grid.

In a preferred embodiment, the aperture defining structure defines a first and a second in-plane vector that are parallel to a slab of material that is not transparent (examples are metals such as gold (Au), silver (Ag), chromium (Cr), aluminium (Al)). The first (smallest) in-plane aperture dimension is parallel to the first in-plane vector and the second (largest) in-plane aperture dimension is parallel to the second in-plane vector.

In addition, the apertures define a second in-plane dimension W2 above the diffraction limit and there is a transmission plane that is composed of the first in-plane vector and a third vector that is normal to the first and second in-plane vectors and a reflection plane that is composed of the second in-plane vector and the aforementioned third vector. R-polarized incident light, that is light having an electric field orthogonal to the plane of transmission, is substantially reflected by the aperture defining structure and generates an evanescent field inside the aperture. T-polarized light incident on an aperture defining structure according to the present invention, that is light having an electric field parallel to the planes of transmission of the one or more apertures, is substantially transmitted by the aperture defining structure and generates a propagating field inside the aperture.

In some embodiments, the sensor comprises a carrier with a binding surface at which target components can collect. The term "binding surface" is chosen here primarily as a unique reference to a particular part of the surface of the carrier, and though the target components will in many applications actually bind to said surface, this does not necessarily need to be the case. All that is required is that the target components can reach the binding surface to collect there (typically in concentrations determined by parameters associated to the target components, to their interaction with the binding surface, to their mobility and the like). The carrier preferably has a high transparency for light of a given spectral range, particularly light emitted by the light source that will be defined below. The carrier may for example be produced from glass or some transparent plastic. The carrier may be permeable; it provides a carrying function for aperture defining structures provided on the carrier having a smallest in plane aperture dimension (W1) smaller than a diffraction limit.

b) A source for emitting a beam of radiation, called "incident light beam" in the following, into the aforementioned carrier such that it is at least partly reflected, at least in an investigation region at the binding surface of the carrier. The light source may for example be a laser or a light emitting diode (LED), optionally provided with some optics for shaping and directing the incident light beam. The "investigation region" may be a sub-region of the binding surface or comprise the complete binding surface; it will typically have the shape of a spot that is illuminated by the incident light beam. The aperture defining structure causing at least R polarized light to be reflected. In response to the R polarized component of the radiation incident at the structure, evanescent radiation is generated in a detection volume formed between the apertures. Optionally, the detection volume may be extending into a volume formed between the aperture defining structures and the carrier.

c) A detector for determining radiation from the target component present in the detection volume, in response to the emitted incident radiation from the source. The detector may comprise any suitable sensor or plurality of sensors by which light of a given spectrum can be detected, for example a photodiode, a photo resistor, a photocell, or a photo multiplier tube. Where in this specification the term light or radiation is used, it is meant to encompass all types of electromagnetic radiation, in particular, depending on context, as well visible as non visible electromagnetic radiation.

The microelectronic sensor device may be used for a qualitative detection of target components, yielding for example a simple binary response with respect to a particular target molecule ("present" or "not-present"). Preferably the sensor device comprises however an evaluation module for quantitatively determining the amount of target components in the investigation region from the detected reflected light. This can for example be based on the fact that the amount of light in an evanescent light wave, that is absorbed or scattered by target components, is proportional to the concentration of these target components in the investigation region. The amount of target components in the investigation region may in turn be indicative of the concentration of these components in a sample fluid that is in communication with the aperture according to the kinetics of the related binding processes.

Turning to FIG. 1 a general setup is shown of a microelectronic sensor device 100. A central component of this device is the carrier 11 that may for example be made from glass or transparent plastic like polystyrene. The carrier 11 is located next to a sample chamber 2 in which a sample fluid with target components to be detected (e.g. drugs, antibodies, DNA, etc.) can be provided. Chamber 2 may in addition be defined by upstanding walls 111 that, in a preferred embodiment, are repeated continuously to form a plurality of adjacent walls 111, forming a well-plate for example, for microbiological assays. The sample further comprises particles 10, for example electrically charged or fluorescent particles, wherein these particles 10 are usually functionalized with binding sites (e.g., antibodies) for specific binding of aforementioned target components (for simplicity only the particles 10 are shown in the Figure). Other label particles, for example superparamagnetic beads, could be used as well.

In this embodiment, the interface between the carrier 11 and the sample chamber 2 is formed by a surface called "binding surface" 12. This binding surface 12 may optionally be coated with capture elements, e.g. antibodies, ligands, which can specifically bind the target components.

The sensor device 100 further comprises a light source 21, for example a laser or a LED, that generates an incident light beam 101 which is transmitted into the carrier 11. The incident light beam 101 arrives at the binding surface 12. Radiation from the target component 102 leaves the carrier 11 and is detected by a light detector 310, e.g. a photodiode. Alternatively, the light detector 310 may determine the power/energy of the reflected light beam 102 (e.g. expressed by the light intensity of this light beam in the whole spectrum or a certain part of the spectrum). The measurement results are evaluated and optionally monitored over an observation period by an evaluation and recording module 32 that is coupled to the detector 310. On the carrier surface 12, a slab of material that is not transparent, preferably metal (for example gold (Au), silver (Ag), chromium (Cr), aluminium (Al)) is provided in the form of strips 20, defining a wire grid having a smallest in plane aperture dimension (W1) smaller than a diffraction limit, the diffraction limit defined by the ratio between wavelength and twice the refractive index of the medium 2 containing the target components 10. The angle of incidence α2 can in principle vary from 0 to 90°. It is noted that the plane of incidence is in the plane of paper as shown in FIG. 1. Due to the diffraction limited nature of the aperture, in investigation volume 13 (see FIG. 2) an evanescent field is created that may be selectively disturbed due to the presence of particles that are bound by carrier surface 12 or at least within reach of the evanescent field generated by the aperture defining structures 20 in the detection volume 4.

FIG. 1 shows that the surface is provided with a plurality of aperture defining structures (20). In particular, in the shown embodiment, these structures can be provided by metal wires or strips (20), defining apertures W1. Typically, these strips are formed as a periodic structure of elongated parallel wires (20). Such a structure is typically referenced as a wire grid. Although the invention can be applied in a periodic structure (grating structure), this is not necessary, indeed the structure may also be aperiodic or quasi periodic. The aperture dimension (W1) of the smallest dimension, or, if applicable, a grating period Λ, is typically smaller than the diffraction limit, the diffraction limit defined by a principal wavelength or band of wavelengths of the incident light beam and a medium for containing the target components. Preferably, the incident light beam is exclusively comprised of radiation having wavelengths above the diffraction limited wavelength, which is defined as twice the smallest aperture dimension (W1) times the refractive index of the medium (2) containing the target components (10). A nice property of aperture defining structures such as the wire-grid technology is that the light inside the aperture can be switched from an evanescent mode (as depicted in FIG. 2) to a propagating mode quite easily by switching the polarization of the input light, which enables both surface specific and bulk measurements.

Typical sizes of the beads 10 are in the order of 10-1000 nm. Typical parameters for a wire grid made of Aluminium used for red excitation light (e.g., HeNe laser having a wavelength of 632.8 nm) are a period of 140 nm (50% of the diffraction limit in water for this wavelength); duty cycle of 50% and a height of 160 nm. For these parameters, the (1/e) intensity decay length in an aperture filled with water is only 17 nm. The maximum bead size (i.e., beads that 'just' fit in the space between the wires) is limited to somewhat smaller than 70 nm for these parameters.

As an example, consider the case of beads with a diameter of 200 nm. For this diameter, a period of 580 nm and a duty cycle of ⅔ is a reasonable choice; opening between the wires of 387 nm. In order to avoid propagating diffraction orders for the transmitted light, the grating period should be below the diffraction limit in water (index of refraction of 1.33): for a period of 580 nm, this implies that the wavelength of the incident light is at least 1540 nm. For a wavelength of 1600 nm and a thickness of 600 nm, this results in an (1/e) intensity decay length of 109 nm and a background suppression (for the bulk on top of the wire grid) of 250.

Figure 2:
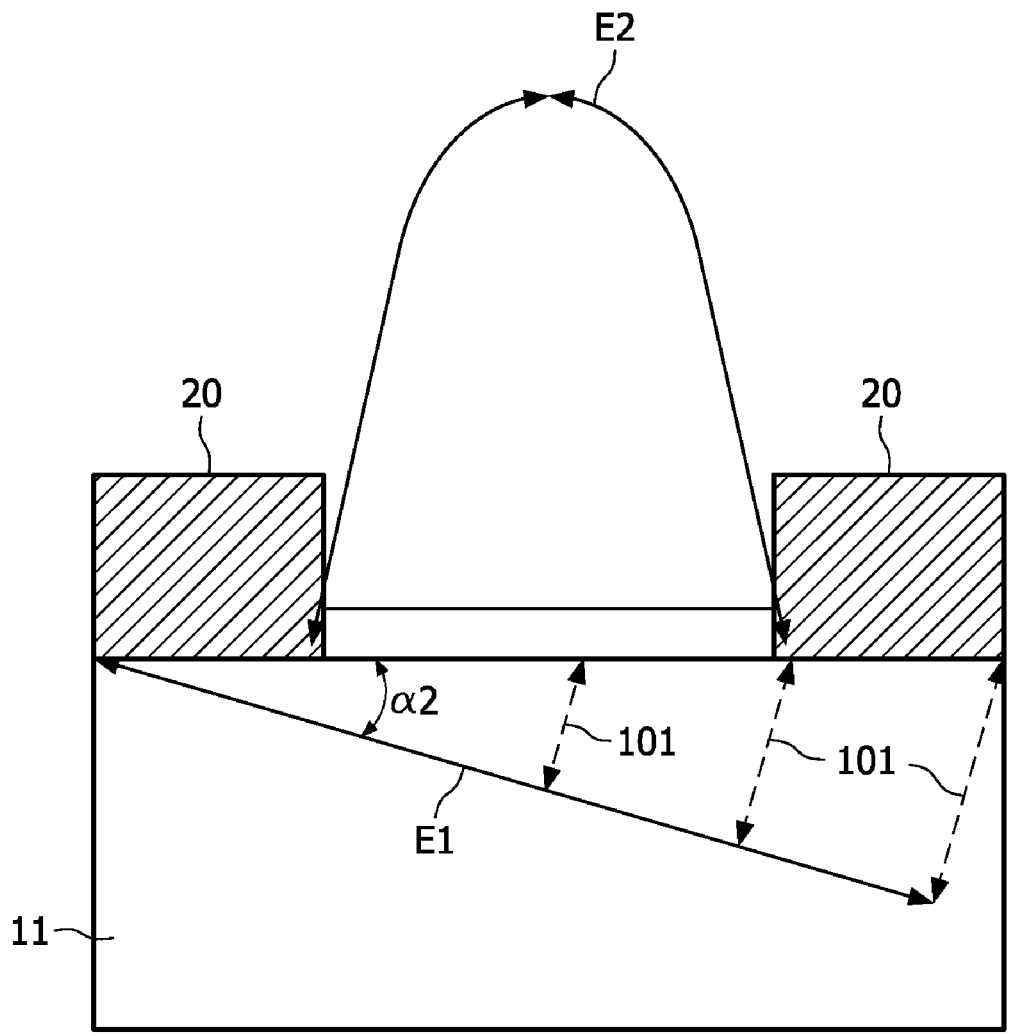
FIG. 2 shows an illustrative schematic detail the field distribution incident on the sensor device of FIG. 1.

FIG. 2 shows investigation region 13 of FIG. 1 in more detail. It follows that a sub-optimal evanescent excitation intensity is due to the fact that the phase front of the incoming light is not necessarily parallel to the phase front of the evanescent mode propagating through the slit(s) of the wire grid. The excitation efficiency (that is the fraction of the incident power that is converted into an evanescent mode of the slit) is roughly proportional to the overlap integral between the projection of the incident electric field (E1; which is a plane wave that propagates under an angle (α2) with respect to the normal of the substrate-wire grid interface) on the input facet of the wire grid and the electric field of the fundamental evanescent mode of the slit (E2), which implies that the excitation efficiency is proportional to cos(α2) and proportional to a pre-factor smaller than unity that accounts for the variation of the phase of the projection of the incident field along the in plane dimension W1. As a consequence the excitation efficiency decreases with increasing angle α2.

The plane of incidence of incident beam (101) in FIG. 2 lies in the plane of paper, for clarity reasons, the reflective beam is not shown. The plane of incidence is accordingly parallel to the smallest width dimension of the aperture defining structures—metallic wires (20) and parallel to a third vector pointing in a direction that is normal to a first vector pointing in the smallest width direction and a second vector pointing in the largest width direction of the aperture. Because the plane of incidence is orthogonal to the largest in plane aperture dimension W2 (which is oriented in a direction perpendicular to the plane of paper see FIG. 3) and parallel to the smallest in plane aperture dimension W1, the excitation efficiency of the evanescent mode (E2) that is formed between the apertures (20) is reduced by a cosine factor and the aforementioned pre-factor depending on the angle of incidence (α2) formed between the phase front (E1) of the incident radiation (101) and the phase front of the evanescent mode (E2). The plane wave (field distribution, E1) is incident via the substrate (1) on a wire grid with wires (20). Each slit between the wires 20 supports an evanescent mode (field distribution, E2) that is excited by the incident plane wave that propagates under an angle (α2).

Figure 3:
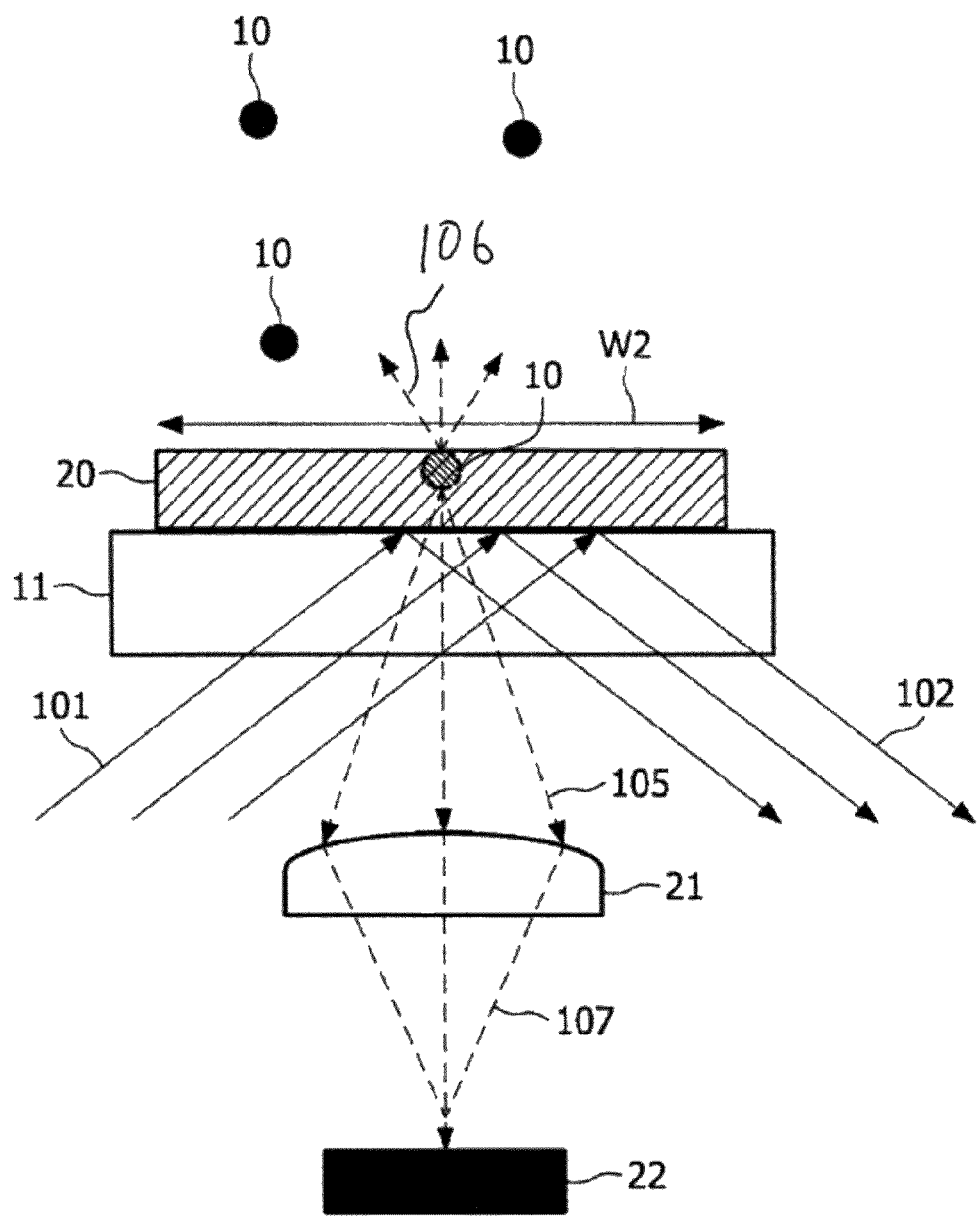
FIG. 3 schematically shows an embodiment according to the invention.

FIG. 3 shows a first embodiment according to an aspect of the invention. In this schematic drawing, the bead (10) that is within detection volume (not shown) between strips (20) is illustrated in see-through mode. In this embodiment an increased scattering due to presence of beads (10) in the evanescent volume is measured. Alternatively, other types of radiation from target component (10) could be measured, for instance, the target could be luminescent. In this embodiment the detector (22) is arranged to detect a radiation (105) from the target (10). The beam (105) is imaged through a lens (21) on detector surface (22) and is accordingly separated from specularly reflected light beam (102) to indicate a presence of a target component (10). In particular, a presence of the bead (10) in the evanescent field results in scattering (105, 106). In particular, by orienting the detection opening (22) away from the specularly reflected beam (102), the reflected light is spatially separated from the scattered light (105), by illuminating the wire grid under an angle larger than the Numerical Aperture (NA) of the imaging lens (21). When using the wire grid in this reflection mode i.e. illumination of the wire grid sample under an angle that is not normal with the normal of the substrate and has an angle that is outside the NA of the lens (21) for collecting the generated scattering or fluorescence, the phase front of the incoming light (101) is parallel with the phase front of the evanescent mode supported by the slit, due to the beam 101 being incident on carrier 11 and evanescent field generating structure 20 in a plane of incidence parallel to the largest in plane aperture dimension (W2) and parallel to a third vector that is normal to the smallest (W1) and largest (W2) in-plane dimensions. As a result the detected evanescent excitation power/intensity is improved.

The problem of reduced excitation efficiency due to the angle between the incident wave and the evanescent mode of the slit accordingly can be solved by realizing that the wave fronts of the incident wave and the evanescent mode of the slit are substantially parallel and having a polarization transverse to the plane of transmission (defined by a first vector in the direction of W1 and a third vector normal to directions W1 and W2) of the aperture defining structure. This boils down to a plane of incidence that is substantially parallel to the reflection plane of the aperture defining structure and a polarization substantially parallel to the plane of incidence.

An additional advantage of this configuration is that the incident light is TM polarized with respect to the interface between the substrate and medium in front of the substrate (which is typically air).

The Brewster angle at an interface is given by [2]:

$$\tan(\alpha 1) = \frac{n_{substrate}}{n_{incident}}. \quad (2)$$

With $n_{substrate}$ and $n_{incident}$ as the refractive indexes of the substrate and the incident medium (in most cases air). Using Snell's law, it can be demonstrated that light incident at the Brewster angle results in light in the substrate that propagates at the Brewster angle for the substrate-air interface. In other words illumination at the Brewster angle results in zero reflection at the incident medium (air)-substrate and the substrate-incident medium (air) interfaces. Accordingly, the optical guiding device (21, 31) is arranged to provide a plane of incidence being along the largest in plane aperture dimension and along the out of plane normal direction. The term 'along' here is used to indicate that the directions are substantially parallel to the largest in plane aperture direction and the out of plane normal direction, that is, preferably within 10 degrees, more preferably within 5 degrees, most preferably within 1 degree from the said directions.

Figure 4:
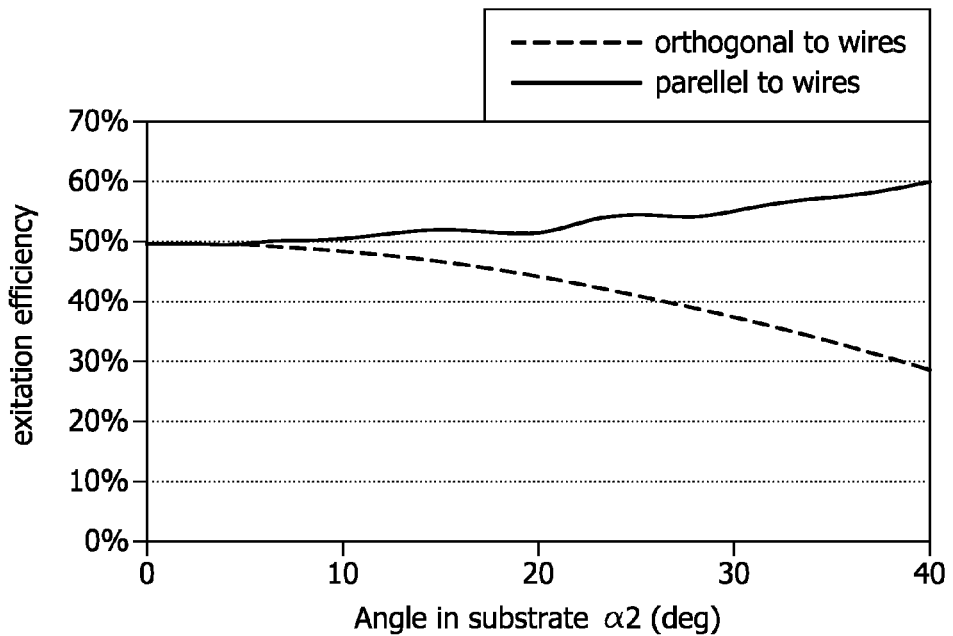
FIG. 4 schematically shows an illustrative graph of the excitation efficiency for varying planes of incidence.

FIG. 4 shows a graph illustrating the excitation efficiency of evanescent mode for a planes of incidence that are substantially parallel to the normal of the substrate wire grid interface and normal to the wires (dashed line) and substantially parallel to the wires (solid line) of a wire grid. In this example the wire grid is formed by aluminum wires having a period 140 nm and duty cycle of 50%. The wire grid is provided on a glass substrate; with water on top of the wire grid and illuminated by radiation having a wavelength of 632.8 nm. It is shown that the excitation efficiency is optimal for a plane of incidence substantially parallel to both the normal of the interface between the wire grid and the substrate and substantially parallel to the wires of the wire grid and—of course—an electric field substantially parallel to the plane of incidence. For an angle of incidence roughly equal to the Brewster's angle ($\alpha 2$=34.5 degrees) a plane of incidence parallel to the wires and the normal results in an excitation efficiency of 57%, which is actually slightly larger than the duty cycle of the wire grid.

Figure 5:
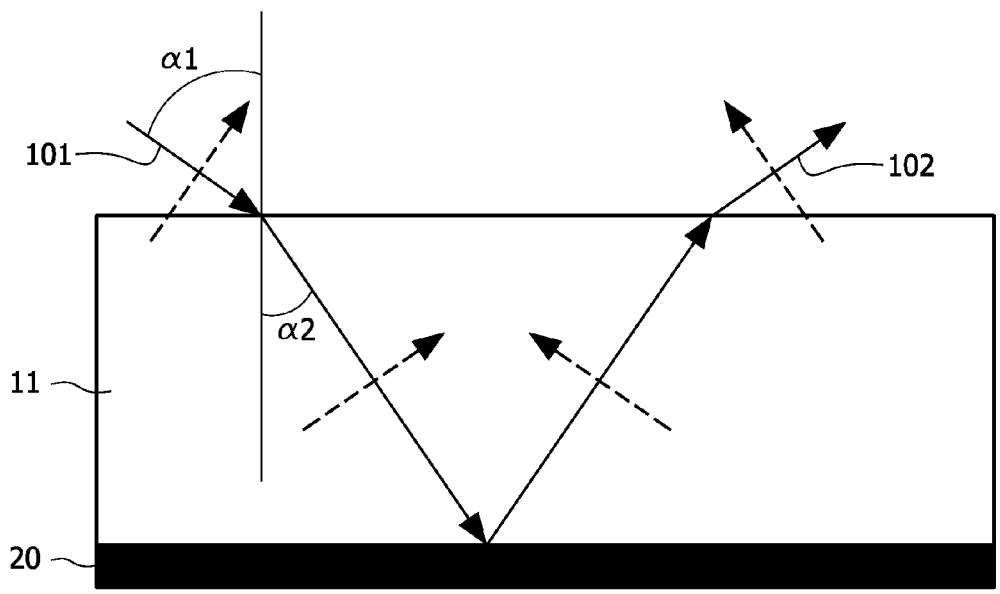
FIG. 5 shows schematically a ray path for incident light according to a preferred embodiment.

FIG. 5 shows an embodiment, where the parasitic reflections are minimized for incident beam 101. To this end, preferably the angle of incidence between the direction of incidence and the normal direction is set to provide polarized radiation where the electric field vector is along the plane of incidence, that is, preferably, an angle between the electric field of the polarized radiation and the plane of incidence is less than 10 degrees; more preferably less than 5 degrees; most preferably less than 1 degree. Typically, this results in having, relative to the plane of incidence an out of plane electric field vector of an intensity less than 2% of the total intensity, which can be typically provided by an angle of incidence equal to or in a range of 7° about the Brewster angle. Accordingly, by setting the angle of the incident light $\alpha 1$ to about the Brewster angle of the air-substrate interface, by setting a plane of incidence substantially parallel to the wires and the normal of the interface between the aperture defining structure (wires), and by having a polarization of the incident light that is substantially parallel to the plane of incidence, parasitic reflections are minimized and the intensity of the excitation light is optimized. The parasitic multiple reflections at the interface between the substrate and the medium in front of the substrate, that would otherwise occur, can be suppressed by realizing that for TM polarized light (i.e., electric field in the plane of incidence formed between incident beam 101 and reflected beam 102) and a given set of refractive indexes there is an angle (the so-called Brewster angle) where the reflection is zero. So, an arrangement for suppression of parasitic reflections is to illuminate the wire grid sample with light under the Brewster angle and polarized such that the electric field is in the plane of incidence. Generation of evanescent fields in the space between the wires of the wire grid requires that the components of the electric field are substantially parallel to the plane of reflection of the wire grid. This implies that the parasitic reflections can be eliminated by an arrangement where the plane of incidence (the plane of incidence is substantially parallel to the wave vectors of the incident, reflected (102) and transmitted light) is substantially parallel to the normal to the interface between the wire grid and the substrate (11) and substantially parallel to the largest dimension (W2) of the aperture defining structure (i.e., the wires 20) of the wire grid.

The dashed arrows indicate an orientation of the electric field that is in the plane of incidence (the plane of the paper) and whose projections on the plane parallel to the substrate (normal to the plane of the paper) are parallel to the long (above the diffraction limit) in-plane direction of the wires (20) of the wire grid.

Figure 6:
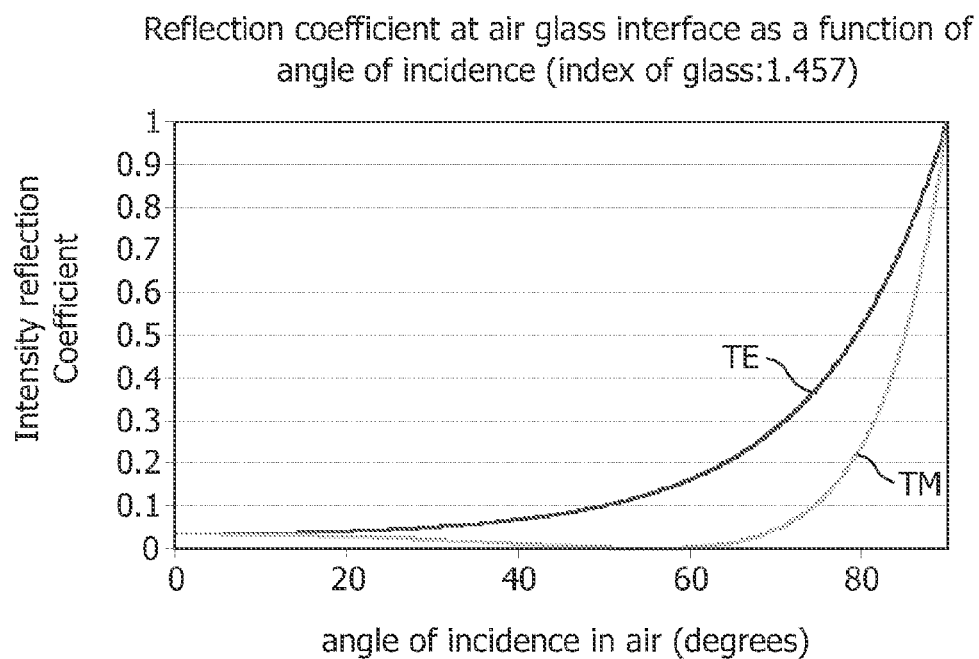
FIG. 6 shows the intensity reflection coefficients for polarized light incident on glass air interface.
Figure 6:
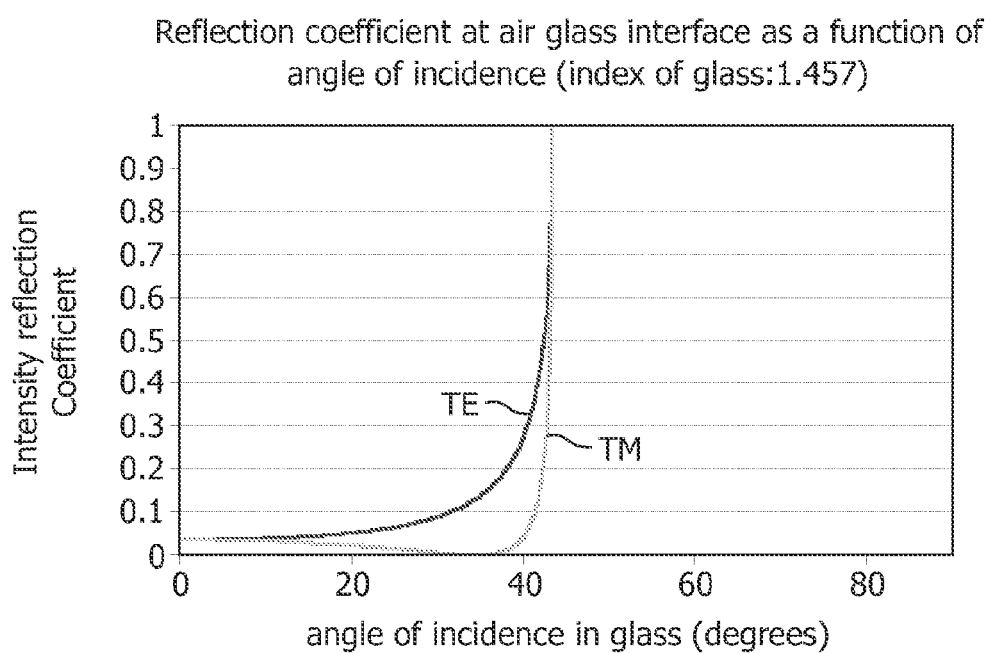

FIG. 6 gives an example of the intensity reflection coefficients for TE and TM polarized light as a function of the angle of incidence for air-glass and glass-air interfaces. For a substrate of glass with an index of refraction (1.457) and light incident via air, we find a Brewster angle at the air-substrate interface of 55.7 degrees and at the substrate-air interface of 34.5 degrees. Using the fact that the magnitude of the reflection coefficients at the incident medium-substrate and substrate-incident medium interfaces are identical for given angles of propagation in the incident medium and the substrate, it can be seen that the reflection coefficients is very small (less than 1%) for incident angles $\alpha 1$ between 42-64 degrees. For TE polarized light, the reflection coefficients are substantially higher; 7-20% (for angles of incidence of 42-64 degrees).

Hence preferably, for a configuration where i) the plane of incidence is parallel to the normal of the interface between the aperture defining structures (i.e wires) and the substrate and parallel to second dimension of the aperture defining structures (that is along the long direction of the wires) of the wire grid; ii) a polarization such that the electric field is parallel to the plane of incidence; and iii) an angle of incidence close to the Brewster's angle parasitic spurious reflections can be minimized and the excitation efficiency (for that particular angle of incidence) can be optimized.

Figure 7:
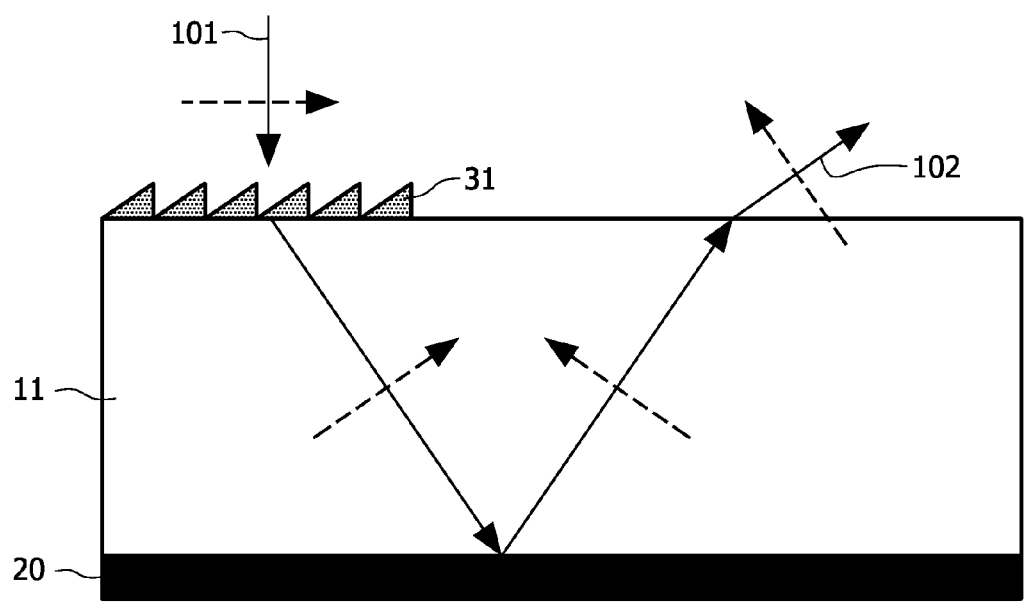
FIG. 7 shows schematically a preferred embodiment according to an aspect of the invention.

FIG. 7 shows an alternative embodiment wherein a grating is used to convert angle of incident light to angle equal to around the Brewster angle. In particular, grating (31) is attached to a top face of transparent carrier (11). The grating order corresponds with the Brewster angle for the interface of carrier 11. In this way, the incident beam 101 is guided via grating 31 towards the aperture defining structures (20) fixed the opposite site of carrier (11). For reasons of clarity, only a single transmission order of the grating 31 is shown in the figure. Matching of a grating order (m) with the Brewster angle defines the grating period, assuming normal incident light:

$$\Lambda = m\lambda \frac{\sqrt{n_{incident}^2 + n_{substrate}^2}}{n_{incident} n_{substrate}} \quad (3)$$

For an incident wavelength of l=632.8 nm and a glass substrate with index nsubstrate=1.457, this results in a grating period Λ=768 nm in order to match the first order with the Brewster angle of the grating. By tuning the thickness and shape of the grating, one can optimize the diffraction pattern such that the fundamental order (m=0) is minimized.

As an example, for a blazed grating with a height of 1500 nm we find a minimum in the diffraction efficiency of 27.5% the fundamental order and a maximum in the diffraction efficiency of the positive first order (m=+1) of 68.5% and only 4% in the negative first order (m=−1).

The device and method according to the invention can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Other variations to the disclosed embodiments can be understood and effected by those skilled in the art in practicing the claimed invention, from a study of the drawings, the disclosure, and the appended claims. Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An optical device for providing evanescent radiation, in response to incident radiation, the optical device comprising:
   a sample chamber having a detection volume for containing a target component in a medium, the detection volume having at least one in-plane dimension smaller than a diffraction limit, the diffraction limit defined by a radiation wavelength of the incident radiation and the medium;
   aperture defining structures for providing the evanescent radiation, the aperture defining structures having a smallest in plane aperture dimension smaller than the diffraction limit, wherein the detection volume is provided between said aperture defining structures, wherein the aperture defining structures further define a largest in plane aperture dimension, and wherein said largest in plane aperture dimension is larger than said diffraction limit;
   an optical guiding device for guiding a beam of radiation having a wavelength to have a direction of incidence on the optical device different from an out of plane normal direction for providing the incident radiation incident at the optical device, for providing the evanescent radiation in the detection volume in response to the incident radiation, wherein the optical guiding device is arranged to provide a plane of incidence along both the largest in plane aperture dimension and the out of plane normal direction; and
   a carrier having a first surface where the aperture defining structures are fixed, the carrier having a second surface opposite the first surface, wherein the guiding device comprises a grating fixed to the second surface.

2. The optical device according to claim 1, wherein the aperture defining structures comprise non-transparent material.

3. The optical device according to claim 1, wherein the optical guiding device is arranged to provide polarized radiation having an electric field vector along the plane of incidence.

4. The optical device according to claim 3, wherein the optical guiding device is arranged to set an angle of incidence between the direction of incidence and the out of plane normal direction, in a range of +/−7 degrees from a Brewster angle.

5. The optical device according to claim 1, wherein the guiding device further comprises a source setting device to set a source for providing the incident beam of radiation relative to the optical device.

6. The optical device according to claim 1, being arranged such that the detection volume is extending into the carrier.

7. The optical device according to claim 1, wherein the target components are selected form the group of luminescent particles, absorbing particles, or particles having an index of refraction different from the medium index of refraction.

8. A microelectronic sensor comprising an optical device according to claim 1, further comprising a source to provide the beam of incident radiation, and a detector for detecting radiation from the target component present in the detection volume, in response to the emitted incident radiation from the source.

9. The microelectronic sensor according to claim 8, wherein the detector is arranged to collect radiation from the target component over collection angles smaller than the angle of incidence between the direction of incidence and the normal direction.

10. A method for detecting target component in a detection volume formed in an aperture included at a first surface of a carrier, the method comprising the acts of:
   guiding, by a grating fixed to a second surface of the carrier, a beam of incident radiation having a wavelength to be incident at the optical device and to have a direction of incidence different from an out of plane normal direction, wherein the second surface opposite the first surface;
   providing evanescent radiation, in response to the incident radiation, in a detection volume for containing a target component in a medium, the detection volume having at least one in-plane dimension smaller than a diffraction limit, the diffraction limit defined by the radiation wavelength and the medium, wherein the evanescent radiation is provided by aperture defining structures having the aperture and having a smallest in plane aperture dimension smaller than the diffraction limit, and wherein the detection volume is provided between said aperture defining structures, wherein the aperture defining structures in addition define a largest in plane aperture dimension; wherein said largest in plane aperture dimension is larger than the diffraction limit; and
   detecting radiation from the target component present in the detection volume, in response to the incident radiation emitted from a source;

wherein the plane of incidence is parallel to the largest in plane aperture dimension.

11. The optical device of claim 1, wherein the diffraction limit is a wavelength of the incident radiation in vacuum and divided by twice a refractive index of the medium.

12. The method of claim 10, wherein the diffraction limit is a wavelength of the incident radiation in vacuum and divided by twice a refractive index of the medium.

* * * * *